United States Patent [19]
Montagna

[11] 4,062,902
[45] Dec. 13, 1977

[54] SELECTIVE HYDROGENATION OF CYCLOPENTADIENE USING A PRESULFIDED MOLYBDENUM CATALYST

[75] Inventor: Angelo A. Montagna, Fox Chapel, Pa.

[73] Assignee: Gulf Research & Development Company, Pittsburgh, Pa.

[21] Appl. No.: 748,711

[22] Filed: Dec. 8, 1976

[51] Int. Cl.$^2$ .......................... C07C 5/16; C07C 13/12
[52] U.S. Cl. .............................. 260/666 A; 260/683.9
[58] Field of Search .................... 260/666 A, 683.9

[56] References Cited

U.S. PATENT DOCUMENTS

| | | | |
|---|---|---|---|
| 2,793,238 | 5/1957 | Banes et al. | 260/666 A |
| 3,751,497 | 8/1973 | Schwerdtel et al. | 260/666 A |

*Primary Examiner*—Veronica O'Keefe

[57] ABSTRACT

There is disclosed a method for the selective hydrogenation of cyclopentadiene which comprises contacting cyclopentadiene with hydrogen in the presence of a catalyst consisting essentially of presulfided molybdenum on alumina, and wherein the amount of molybdenum on said catalyst is from 0.52 to 1.18 × 10$^{-3}$ gram atoms of Mo per 100 m$^2$ of said alumina surface.

8 Claims, 1 Drawing Figure

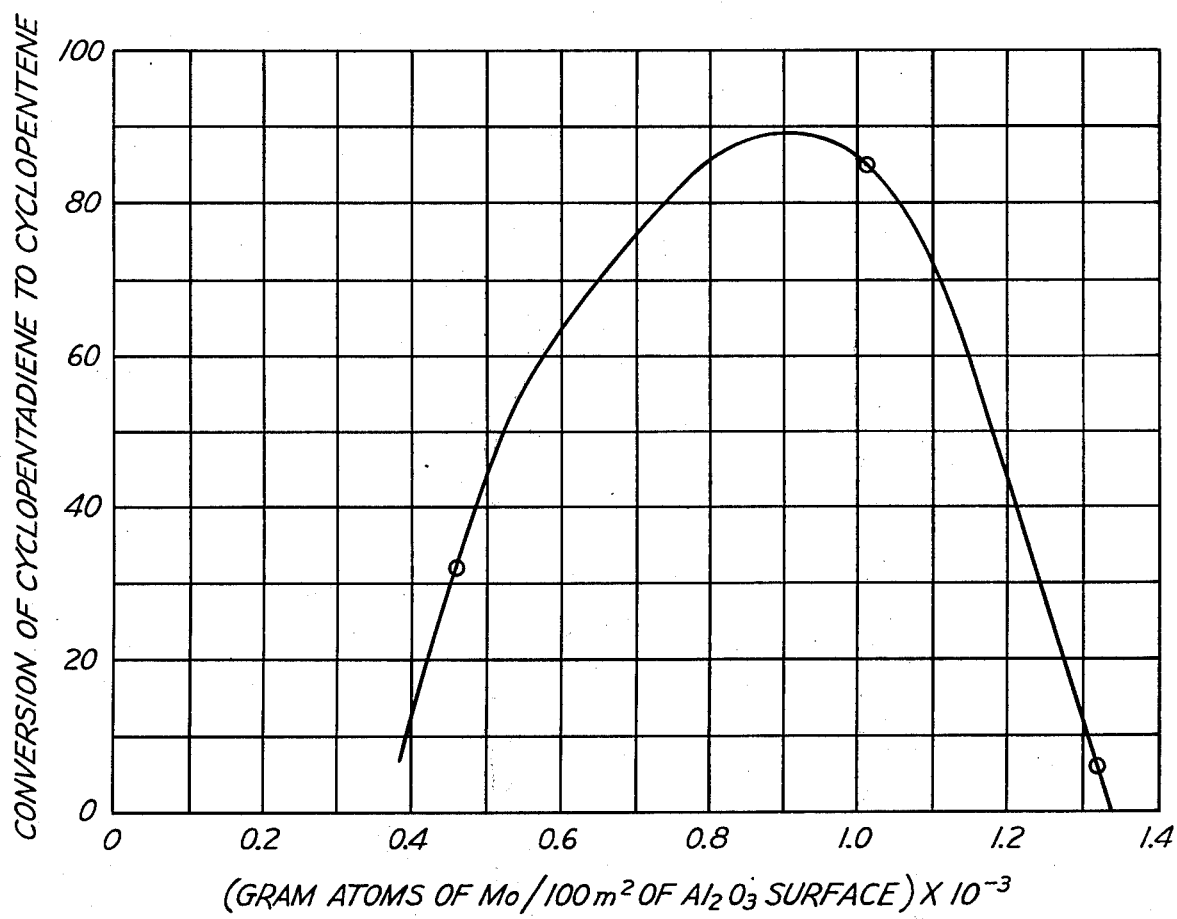

SELECTIVE HYDROGENATION OF CYCLOPENTADIENE USING A PRESULFIDED MOLYBDENUM CATALYST

This invention is directed to the selective hydrogenation of cyclopentadiene to cyclopentene. More specifically, this invention is directed to a process whereby cyclopentadiene is selectively hydrogenated to cyclopentene by contacting a mixture of cyclopentadiene and hydrogen with a catalyst consisting essentially of presulfided molybdenum on alumina.

Dicyclopentadiene, as well as its monomer, cyclopentadiene, is a by-product of the thermal cracking of ethane and propane for olefin production and the pyrolysis of naphtha for ethylene production. The use of these by-products for preparing high-grade chemicals, and in particular cyclopentene, is of commercial significance since cyclopentene is an important monomer in the rubber industry. Normally, however, the catalysts of the prior art do not possess sufficient activity and/or selectivity so that the product from the hydrogenation of cyclopentadiene contains not only the desirable cyclopentene but also some desirable amounts of cyclopentane. Rather expensive distillation equipment is then required to separate the cyclopentene from the cyclopentane in the product stream. It is therefore highly desirable to develop a catalyst with reasonable activity which has a 100 percent selectivity in the conversion of cyclopentadiene to cyclopentene.

In accordance with the invention an improved process for the selective conversion of cyclopentadiene to cyclopentene has now been discovered which comprises contacting the cyclopentadiene plus hydrogen with a catalyst consisting essentially of presulfided molybdenum on alumina and wherein the amount of molybdenum on the catalyst is from 0.52 to 1.18 $\times$ 10$^{-3}$ gram atoms of molybdenum per 100 m$^2$ of said alumina surface.

The cyclopentadiene charge stock for use in the subject reaction can come from any suitable source. As noted above, cyclopentadiene is a product of the thermal cracking of ethane and propane and also the pyrolysis of naphtha for ethylene production. Another by-product is dicyclopentadiene which can be thermally cracked to produce cyclopentadiene.

Cyclopentadiene can be directly hydrogenated in the presence of hydrogen using a suitable catalyst to produce cyclopentene and cyclopentane. The selection of the process conditions and to a large extent the catalysts employed determines the distribution of cyclopentene and cyclopentane in the product. At room temperature the equilibrium constant strongly favors the production of cyclopentane. The production of cyclopentene is not favored thermodynamically until temperatures in excess of 500° C. (932° F.) are employed where, of course, coking becomes a serious problem using a heterogeneous type catalyst. In accordance with this invention, a catalyst has been found which minimizes the rate of the thermodynamically favorable hydrogenation of cyclopentadiene to cyclopentane and results in the production of substantially pure cyclopentene from cyclopentadiene.

It has been discovered that a catalyst consisting essentially of molybdenum on an alumina support is a highly active and selective catalyst for the production of cyclopentene from cyclopentadiene when the amount of molybdenum on said catalyst is from 0.52 to 1.18 $\times$ 10$^{-3}$ gram atoms of molybdenum per 100 m$^2$ of said alumina support, and provided that the molybdenum on alumina catalyst is presulfided and maintained in its sulfided state during reaction. When the catalyst of this invention is employed, side reactions such as polymerization and cracking which foul the catalyst and shorten its life are minimized.

The support for the catalyst of this invention is a substantially pure, high surface area alumina. In general the surface area can be from 50 to 400 m$^2$/g, but is preferably in the range of 100 to 300 m$^2$/g. The alumina can have nominal amounts of impurities such as up to about one percent phosphate and can also be silica-stabilized with up to about five percent silica. Other small amounts of inorganic oxides such as one percent magnesium oxide can also be present if desired.

The catalyst of this invention consists essentially of the above-described alumina having molybdenum distended substantially uniformly on the surface of the alumina support in a concentration from 0.52 to 1.18 $\times$ 10$^{-3}$ gram atoms of molybdenum per 100 m$^2$ of surface area of said alumina; preferably from 0.65 to 1.1 $\times$ 10$^{-3}$ gram atoms of molybdenum per 100 m$^2$ of surface face area of said alumina. In any given instance, the amount of molybdenum in weight percent to employ will depend upon the surface area of the alumina which is chosen as the support. Obviously aluminas having a higher surface area will require more molybdenum to obtain the desired surface coverage in terms of gram atoms of molybdenum per 100 m$^2$ of the alumina. Using the preferred alumina supports of this invention, i.e., those having 100 to 300 m$^2$/g, the amount of molybdenum of the finished catalyst is generally within the range of about 5 to 25 weight percent molybdenum (expressed as the zero valent metal) in order to form a catalyst having the above-defined range of gram atoms of molybdenum per 100 m$^2$ of Al$_2$O$_3$ surface.

Any technique can be employed to distend the molybdenum in a substantially uniform manner on the surface of the alumina. Such techniques are well known in the art and form no part of this invention. For example, a suitable technique is described in Example 1 of U.S. Pat. No. 3,840,073, and the description is incorporated herein.

After the molybdenum is distended on the surface of the alumina support, the material is normally dried and calcined, and the catalyst is then pretreated with a sulfur compound, for example, H$_2$S or CS$_2$, to convert the molybdenum present to the sulfide form. The particular conditions or technique used for sulfiding are not critical, and any conventional presulfiding technique can be employed. For example, a mixture of 1 to 10 percent H$_2$S in hydrogen can suitably be passed over the catalyst at temperatures of about 350° to 700° F. (117° to 371° C.) and at suitable pressures of perhaps one atmosphere to 500 psig (0.10 to 3.45 MPa) for a sufficient time to convert most of the molybdenum to the sulfided state.

To maintain the catalyst in the sulfided state, it is necessary to add sulfur compounds to the feed, such as H$_2$S, CS$_2$, open-chain sulfides, including alkyl sulfides or cycloalkyl sulfides. The amount of the sulfide compounds on a pure sulfur basis to add to the feed is not critical but is generally on the order of 0.10 to 1.0 weight percent of the feed.

The reaction parameters at which the hydrogenation process of this invention is conducted do not appear to be extremely critical. The reaction temperature is generally 400° to 700° F. (204° to 371° C.), is preferably from 425° to 600° F. (219° to 316° C.), and is most preferably from 450° to 600° F. (232° to 316° C.). In general the reaction is too sluggish at temperatures below 400° F. (204° C.), and too much coking occurs at temperatures above 700° F. (371° C.). The reaction pressure can be from atmospheric to 1000 psig (0.10 to 6.9 MPa) but is preferably from 25 to 600 psig (0.17 to 4.1 MPa), and most preferably from 35 to 300 psig (0.24 to 2.1 MPa). The reaction pressure does not appear to be critical, but sufficient pressure is normally employed to aid in a transfer of the reactants through the reaction system.

The liquid hourly space velocity based on the cyclopentadiene is normally from 0.1 to 20 volumes of cyclopentadiene per volume of catalyst per hour; is preferably from 0.5 to 10 v/v/hr.; and most preferably from 0.7 to 5 v/v/hr.

The standard cubic feet of hydrogen per barrel of cyclopentadiene is preferably at least enough to satisfy the stoichiometry involved, but usually is in the range of 2500 to 20,000; preferably 3,000 to 15,000; and most preferably 5,000 to 12,000 SCF/bbl.

The reaction can suitably occur, for example, by passage of the cyclopentadiene and hydrogen through a fixed bed of the molybdenum on alumina catalyst consisting of particles of a suitable size, either by passage of the reactants and hydrogen upflow or downflow. Because of the high temperature and low pressure conditions employed in the process of this invention, all or substantially all of the cyclopentadiene and products are in the vapor phase. Fluid bed, coil or riser type reactors can also be used if desired.

The invention will be further described with reference to the following experimental work.

Evaluation of the various catalyst samples for their activity and initial aging rate in cyclopentadiene to cyclopentene hydrogenation was carried out in an isothermal gas phase reactor maintained at atmospheric pressure. The feed to the reactor consisted of 9.2% CPD - 89.9% $H_2$-0.9% $H_2S$. The run conditions were 450° F. (232.2° C.), atmospheric pressure (0.10 MPa) and a GHSV of 3300 based on the total gas. The product gas was analyzed by gas chromatography. These runs were generally less than seven hours long.

EXAMPLE 1

55.95 grams of a 20/30 mesh alumina, whose properties are shown in Table 1 below, were contacted with about 59 ml of an aqueous solution containing (i) 21.27 grams of ammonium paramolybdate $((NH_4)_6(Mo_7O_{24}\cdot4H_2O))$ and (ii) 9.30 ml of concentrated ammonium hydroxide. The amount of the solution was just sufficient to bring the alumina support to the point of incipient wetness.

The material was oven dried for 24 hours at 120° C. and then calcined for 10 hours at 538° C.

The amount of molybdenum on the catalyst was calculated to be 16.0 weight percent. By calculation the amount of molybdenum on the support was 1.01 × $10^{-3}$ gram atoms Mo per 100 $m^2$ of $Al_2O_3$ surface.

The catalyst was thereafter presulfided by contacting the molybdenum on alumina material with a flowing stream of hydrogen containing 8 percent by weight $H_2S$ for 1 hour at 600° F. (316° C.).

TABLE 1

| Properties of Alumina Support | |
| --- | --- |
| Surface Area | 196 $m^2$/g |
| Pore Volume | 0.66 cc/g |
| Avg. Pore Radius | 67.3 Å |

TABLE 1-continued

| Properties of Alumina Support | |
| --- | --- |
| Pore Radius (RP) | 83.2 Å |

EXAMPLE 2

The preparation of Example 1 was repeated, except the amount of molybdenum was reduced so that the final catalyst contained only 8 weight percent molybdenum. By calculation, the percent molybdenum on the support was equal to 0.46 × $10^{-3}$ gram atoms of Mo per 100 $m^2$ of $Al_2O_3$ surface. This catalyst was in the form of an extrudate.

EXAMPLE 3

Example 1 was repeated except the amount of molybdenum was increased to 20 weight percent molybdenum on the catalyst, which calculates out to be 1.32 × $10^{-3}$ gram atoms of Mo per 100 $m^2$ of $Al_2O_3$ surface.

A first series of runs was made with the catalysts from Examples 1 through 3 for the conversion of cyclopentadiene to cyclopentene using the procedure described above to determine the activity of the catalyst for this reaction. The results are shown in Table 2 below:

TABLE 2

| Ex. No. | Catalyst | Conversion of Cyclopentadiene to Cyclopentene | Gram Atoms of Mo per 100 $m^2$ of $Al_2O_3$ |
| --- | --- | --- | --- |
| 4 | From Ex. 1 | 85% | 1.01 × $10^{-3}$ |
| 5 | From Ex. 2 | 32% | 0.46 × $10^{-3}$ |
| 6 | From Ex. 3 | 6% | 1.32 × $10^{-3}$ |

Referring to Table 2 above, it can be seen that acceptable conversions of over 50% are only obtained with the catalyst from Example 1, which contained an amount of molybdenum equivalent to 1.01 × $10^{-3}$ gram atoms per 100 $m^2$ of $Al_2O_3$ surface. In Example 3 where the amount of molybdenum exceeded this amount by 30%, only 6% conversion was obtained (too much molybdenum), whereas in Example 2 there was too little molybdenum, resulting in a conversion of only 32%. The results are plotted on the attached FIGURE. Referring to the FIGURE, the ordinate represents the conversion of cyclopentadiene to cyclopentene and the abscessa represents the grams of Mo per 100 $m^2$ $Al_2O_3$ × $10^{-3}$. At conversion levels of about 50%, the gram atoms of Mo × $10^{-3}$ per 100 $m^2$ $Al_2O_3$ from the curve on the attached FIGURE is 0.52 to 1.18. Preferably, conversion levels of at least 70% are desired, and to achieve this a catalyst having 0.65 to 1.1 × $10^{-3}$ gram atoms of Mo per 100 $m^2$ of $Al_2O_3$ surface area is employed.

It was found that the addition of 5 weight percent Ti to the catalyst of Example 1 and used under the conditions of Example 4 resulted in a decrease in conversion of cyclopentadiene to about 40 percent. Similar undesirable results were found when nickel was added to the molybdenum catalyst or when nickel and titanium both were added to molybdenum.

An aging run was made with the catalyst of Example 1 wherein cyclopentadiene plus hydrogen (10,000 SCF/bbl of cyclopentadiene) were charged downflow through a fixed bed of the molybdenum-alumina presulfided catalyst of Example 1. The reaction conditions included initial temperature of 450° F. (232° C) and a pressure of 50 psig (0.34 MPa) and a liquid hourly space velocity based on the cyclopentadiene of 1.3. For the entire run, 10,000 SCF of $H_2$ were used per barrel of cyclopentadiene (CPD) feed. The hydrogen gas used in this run contained 1% H$_2$S.

The results of the run are shown in Table 3 below. The temperature was increased to 475° F. (246° C.) after 44 hours; increased to 500° F. (260° C.) after 102 hours; and the pressure was increased to 500° F. (260° C.) after 102 hours; and the pressure was increased to 90 psig (0.62 MPa); and the space velocity to 3000 GHSV after about 120 hours of operation to determine the effect of these variables.

TABLE 3

| Ex. No. | Run Time (Hrs.) | Temperature °F | (°C.) | Pressure psig | (MPa) | LHSV | Conversion of CPD Mole % | Cyclopentene Yield | Cyclopentane Yield |
|---|---|---|---|---|---|---|---|---|---|
| 7 | 16 | 450 | (232) | 50 | (0.34) | 1.3 | 100 | 95 | 5 |
| 8 | 22 | " | " | " | " | " | " | 94 | 6 |
| 9 | 16 | " | " | " | " | " | " | 94 | 0 |
| 10 | 54 | " | " | " | " | " | 64 | 64 | 0 |
| 11 | 62 | " | " | " | " | " | 67 | 67 | 0 |
| 12 | 64 | " | " | " | " | " | 62 | 62 | 0 |
| 13 | 65 | " | " | " | " | " | 66 | 66 | 0 |
| 14 | 70 | " | " | " | " | " | 70 | 70 | 0 |
| 15 | 72 | " | " | " | " | " | 63 | 63 | 0 |
| 16 | 78 | " | " | " | " | " | 66 | 66 | 0 |
| 17 | 86 | " | " | " | " | " | 52 | 52 | 0 |
| 18 | 96 | 475 | (246) | " | " | " | 60 | 60 | 0 |
| 19 | 100 | " | " | " | " | " | 60 | 60 | 0 |
| 20 | 118 | 500 | (260) | " | " | " | 65 | 65 | 0 |
| 21 | 128 | " | " | 90 | (0.62) | 1.7 | 64 | 64 | 0 |

Referring to Table 3, it can be seen that small amounts of cyclopentane are produced at the initial high conversion levels, but the catalyst lines out after about 50 hours of operation; and at conversion levels of below about 80 percent cyclopentadiene, preferably at conversion levels of about 50 to 70 percent cyclopentadiene, the yield of cyclopentene substantially equals the conversion, indicating the substantial absence of any cyclopentane in the product.

Resort may be had to such variations and modifications as fall within the spirit of the invention and the scope of the appended claims.

We claim:

1. A process for the selective hydrogenation of cyclopentadiene to cyclopentene which comprises contacting a charge stock comprising cyclopentadiene and hydrogen with a catalyst consisting essentially of a sulfided form of molybdenum on alumina, the amount of molybdenum on the catalyst being from $0.52 \times 10^{-3}$ to $1.18 \times 10^{-3}$ gram atoms of molybdenum per 100 m$^2$ of alumina surface area.

2. The process of claim 1 wherein the catalyst contains 5 to 25 weight percent molybdenum, expressed as the zero valent metal.

3. The process of claim 1 wherein the alumina has a surface area between 50 and 400 m$^2$/g.

4. The process of claim 2 where the temperature of the reaction is maintained between 400° and 700° F. (204° and 371° C.).

5. The process of claim 4 wherein the pressure is from 0 to 1000 psig (0.10 to 6.9 MPa).

6. The process of claim 5 wherein the spacial rate of the cyclopentadiene is from 0.10 to 20 volumes of liquid cyclopentadiene per volume of catalyst per hour.

7. The process of claim 6 wherein the amount of hydrogen is between 500 and 20,000 SCF/bbl of cyclopentadiene charge stock.

8. The process of claim 7 wherein the charge stock contains a sufficient amount of a sulfur compound to maintain the catalyst in the active state.

* * * * *

UNITED STATES PATENT OFFICE
CERTIFICATE OF CORRECTION

Patent No. 4,062,902  Dated December 13, 1977

Inventor(s) Angelo A. Montagna

It is certified that error appears in the above-identified patent and that said Letters Patent are hereby corrected as shown below:

Col. 5, lines 6 and 7 - delete "and the pressure was increased to 500°F. (260"C.) after 102 hours;"

Col. 6, line 38 - "500" should be --2,500--.

Signed and Sealed this

Twenty-ninth Day of August 1978

[SEAL]

Attest:

RUTH C. MASON
Attesting Officer

DONALD W. BANNER
Commissioner of Patents and Trademarks